United States Patent [19]
Kelly et al.

[11] Patent Number: 5,789,222
[45] Date of Patent: Aug. 4, 1998

[54] P5C REDUCTASE GENE FROM ZALERION ARBORICLOA

[75] Inventors: Rosemarie Kelly, Westfield; Prakash S. Masurekar, Warren; Elizabeth A. Register, Scotch Plains, all of N.J.

[73] Assignee: Merck & Co., Inc., Rahway, N.J.

[21] Appl. No.: 665,716

[22] Filed: Jun. 18, 1996

[51] Int. Cl.$^6$ .................... C12N 9/06; C12N 1/20; C12P 21/06; C07H 21/04

[52] U.S. Cl. .................... 435/191; 435/69.1; 435/252.3; 435/320.1; 530/350; 536/23.1; 536/23.2; 536/23.74

[58] Field of Search .................... 435/191, 69.1, 435/71.1, 183, 252.3, 254.1, 254.11, 320.1; 530/350; 536/23.1, 23.2, 23.74

[56] References Cited

PUBLICATIONS

R. Kelly and E. Register, Gene, 172: pp. 149–153 (1996).
C. R. Davis et al., Mol Gen Genet, 248; pp. 341–350 (1995).
M. C. Brandriss and D. A. Falvey, J. Bacteriology; 174(11); pp. 3782–3788 (Jun. 1992).
A. J. Delauney and D.P.S. Verma, Mol. Gen Genet. 221; pp. 299–305 (1990).
C. L. Williamson and R. D. Slocum, Plant Physiol. 100; pp. 1464–1470 (1992).
A. Savioz et al., Gene. 86; pp. 107–111 (1990).
P. T. Hamilton and J. N. Reeve, Mol Gen Genet, 200; pp. 47–59 (1985).
K. M. Dougherty et al., J. Biological Chemistry, 267 (2); pp. 871–875 (Jan. 15, 1992).
F. C. Gherardini et al., J. Bacteriology, 172(6); pp. 2996–3002 (Jun. 1990).
T. Hoshino et al., Biochemical and Biophysical Res. Comm., 199(1); pp. 410–417 (Feb. 28, 1994).
A. H. Deutch et al., Nucleic Acids Res., 10(23); pp. 7701–7715 (FIG. 2), (1982).
Kelly et al. (1996) Gene 172:149–153.

*Primary Examiner*—Charles L. Patterson, Jr.
*Assistant Examiner*—Tekchand Saidha
*Attorney, Agent, or Firm*—Elliott Korsen; Mark R. Daniel

[57] ABSTRACT

There is disclosed an isolated gene coding for an enzyme involved in proline biosynthesis in *Zalerion arboricola*. There is also disclosed a method of using the gene to produce a strain of *Z. arboricola* containing high titers of a desirable fermentation product.

11 Claims, 4 Drawing Sheets

```
 -46                    TCGAATAATTGAAGTTCTTGATCATTTAGGAGTCTGAAAAGTCAAG

1  ATGGCATCCACAGCAAAGGAGGGGTCAGAATTGACTTTGGCGGTGATAGGTTGTGGTACA
   1   M  A  S  T  A  K  E  G  S  E  L  T  L  A  V  I  G  C  G  T

61  ATGGGCATAGCAATCCTCTCCGGTATCCTAGCATCTCTCGACGAAATCCACGCACCAAAC
  21   M  G  I  A  I  L  S  G  I  L  A  S  L  D  E  I  H  A  P  N

121  TCGCAGTCCTCAGAGACAGACGAAACACCCTCAAAGCTCCCCACCAAATTCATAGCCTGT
  41   S  Q  S  S  E  T  D  E  T  P  S  K  L  P  T  K  F  I  A  C

181  GTCCGCTCACCCAAAGGCGCAGAAAAGATCAAAAAAGCACTCTCACCCTACAAAACCCCC
  61   V  R  S  P  K  G  A  E  K  I  K  K  A  L  S  P  Y  K  T  P

241  GTCAAAATCATCCAAAGCGACAATGTCACCGCCTGTAGAGAGGCAGATGTAGTATTACTA
  81   V  K  I  I  Q  S  D  N  V  T  A  C  R  E  A  D  V  V  L  L

301  GGCTGTAAACCATATATGGCCGAAGGCATATTAGGCGAAGAGGGGATGGTCGACGCGTTA
 101   G  C  K  P  Y  M  A  E  G  I  L  G  E  E  G  M  V  D  A  L

361  AAGGGGAAATTGTTGATTAGCATCCTAGCTGGCGTTCCCGCAGAGCAGATATACGGGTAC
 121   K  G  K  L  L  I  S  I  L  A  G  V  P  A  E  Q  I  Y  G  Y

421  ATGTACGGCAAAACACCAGTGAACCCAGAGAAAGAGGGATTATGTCAAGTCGTGCGAGCA
 141   M  Y  G  K  T  P  V  N  P  E  K  E  G  L  C  Q  V  V  R  A

481  ATGCCAAATACAGCGTCTGGGATCCGGGAATCCATGACTGTGATCGCGACGTCGAGTCCC
 161   M  P  N  T  A  S  G  I  R  E  S  M  T  V  I  A  T  S  S  P

541  CCATTATCAGCTACAACTTCGAGTCTGATAACCTGGATCTTCAAACGCATTGGCGATGTC
 181   P  L  S  A  T  T  S  S  L  I  T  W  I  F  K  R  I  G  D  V

601  GTCCAGCTCCCCGCTGCTACAATGGATGCCAGCACCGCGCTGTGTGGCAGTGGCCCAGCC
 201   V  Q  L  P  A  A  T  M  D  A  S  T  A  L  C  G  S  G  P  A

661  TTTTTTGCGCTCATACTGGAGGCTGCGATTGATGGGGCTGTGGCGATGGGGTTGCCAAGA
 221   F  F  A  L  I  L  E  A  A  I  D  G  A  V  A  M  G  L  P  R

721  GCAGAGGCTCAGAGAATGGCGGCGCAGACTATGAAAGGGGCTGCTGGATTGGTATTGTCT
 241   A  E  A  Q  R  M  A  A  Q  T  M  K  G  A  A  G  L  V  L  S

781  GGAGAGCATCCGGCGTTGCTGAAAGATAAAGTGACTACGCCGGGTGGGTGCACGATAGGT
 261   G  E  H  P  A  L  L  K  D  K  V  T  T  P  G  G  C  T  I  G

841  GGGCTGATGGTGCTGGAAGAAGGAGGGGTGAGAGGGACCGTGGCTAGAGCAGTTAGGGAA
 281   G  L  M  V  L  E  E  G  G  V  R  G  T  V  A  R  A  V  R  E

901  GCTACTGTGGTTGCCAGTCAGCTTGGTAAAGGGGTTCAGGGAGTCAACGGTACACGATTT
 301   A  T  V  V  A  S  Q  L  G  K  G  V  Q  G  V  N  G  T  R  F

961  TGAAACAGCCATACTGCGTAGACACATGTCCAAGGAGTTCTGGGGTATAAAAAGTTGTTC

1021  ATTTATGAAAAAAAAAAAAAAAAAAAAAAAAAAAAAAAAAAAAAAAAAAAAAAAAAAAAA

1081  AAAAAAAAAAAAAAAAAAAA  1101
```

P5C REDUCTASE GENE FROM ZALERION ARBORICLOA

FIELD OF THE INVENTION

The present invention relates to the isolation and sequence analysis of the gene encoding delta[1]-pyrroline-5-carboxylate reductase (P5CR), a gene involved in the biosynthesis of L-proline, from *Zalerion arboricola*. The invention also relates to the use of the gene to construct strains of *Z. arboricola* which produce less of an unwanted homologue of the desired pneumocandin product.

BACKGROUND OF THE INVENTION

*Zalerion arboricola* is a filamentous fungus that produces pneumocandins, a group of echinocandin-like antifungals currently being studied as potential therapeutic agents. Pneumocandins comprise a family of acylated cyclic hexapeptides which have anti-Candida, anti-Pneumocystis, and anti-Aspergillus activity (Fromtling and Abruzzo, 1989. J Antibiotics 42:174'178; Schwartz et al., 1989. J. Antibiotics 42:163–167; Schwartz et al.,1992. J. Antibiotics 45:1853–1866; Schmatz et al.,1990. Proc. Natl. Acad. Sci. 878: 5950–5954; Bernard et al., 1993. Abst. 33rd Intersci. Conf. Antimicrob. Agents Chemother. New Orleans, Louisiana, No. 354; Kurtz et al.,1994. Antimicrob. Agents Chemother. 38:1480–1489). Little is known about the genetics of *Z. arboricola* or other members of the genus Zalerion. In fact, none of the genes of *Z. arboricola* have been reported to be isolated. Recently, there have been developed DNA-mediated transformation systems for this fungus using either hygromycin B resistance as a dominant selectable marker or complementation of a mutant defective in nitrate reductase (Kelly et al., 1994. Curr. Genet. 26:217–224). The availability of transformation systems may facilitate studies of pneumocandin biosynthesis as well as the construction of superior production strains.

Figure 1:
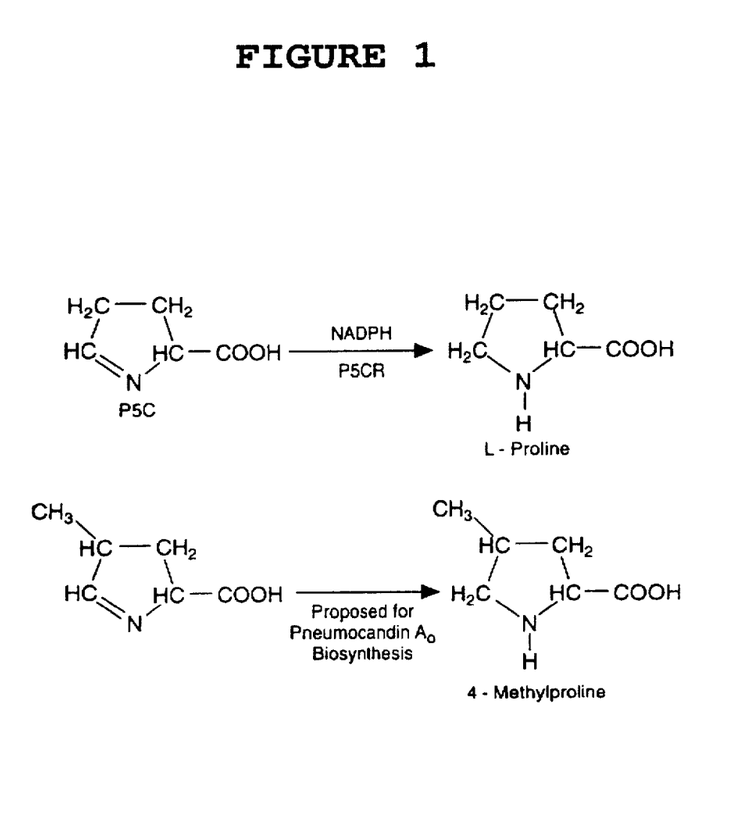
FIG. 1 represents a comparison of the reduction catalyzed by proline biosynthetic enzyme P5CR and reduction proposed for pneumocandin $A_0$ biosynthesis.

The major pneumocandin produced by wild-type *Z. arboricola* is pneumocandin $A_0$, whereas pneumocandin $B_0$ is a minor component of the fermentation (Schwartz et al.,1992. J. Antibiotics 45:1853–1866). Pneumocandin $B_0$ is a precursor of a potent semi-synthetic compound, L-733,560 (Bouffard et al.,1994. J. Med. Chem. 37:222–225). Thus, one objective of the invention is to construct a strain of *Z. arboricola* that produces only pneumocandin $B_0$. Pneumocandin $B_0$ differs from pneumocandin $A_0$ by the presence of a residue of 3-hydroxyproline in place of 3-hydroxy-4-methylproline. Proline is the precursor of 3-hydroxyproline, whereas leucine is the precursor of 3-hydroxy-4-methylproline (Adefarati et al., 1991. J. Amer. Chem. Soc. 113:3542–3545). A pathway for the formation of 3-hydroxy-4-methylproline of pneumocandin $A_0$ was hypothesized by Adefarati et al.,1992 (J. Antibiotics 45:1953–1957); one of the proposed steps is similar to the conversion of delta[1]-pyrroline 5-carboxylic acid (P5C) to proline by P5C reductase (formally called L-proline:NAD(P)$^+$5-oxidoreductase, EC 1.5.1.2) as illustrated in FIG. 1.

As an initial step in determining if P5C reductase is involved in pneumocandin $A_0$ biosynthesis, the P5CR gene from *Z. arboricola* was cloned and characterized. Both cDNA and genomic clones encoding P5CR were isolated. P5CR is a pyridine nucleotide-dependent cytosolic enzyme that is found in all cells and whose primary role is thought to be the final step of proline biosynthesis. Other functions for P5CR have also been proposed. More recent studies indicate that the P5C-dependent oxidation of NADPH increases activity of the hexose monophosphate shunt (Kohl et al., 1988. Proc. Natl. Acad. Sci. 85:2036–2040; Yeh and Phang, 1988. J. Biol. Chem. 263:13083–13089), and other work implicates P5C reductase in the regulation of cellular redox potentials (Phang, 1985. Curr. Top. Cell. Regul. 25:91–132). P5CR genes have been cloned from several organisms and conserved residues have been identified among the predicted amino acid sequences (Deutch et al., 1982. Nucleic Acids Res. 10:7701–7714; Hamilton and Reeve, 1985. Mol. Gen. Genet. 200:47–59; Tomenchok and Brandriss, 1987. J. Bacteriol. 169: 5364–5372; Delauney and Verma, 1990. Mol. Gen. Genet. 221:299–305; Gheradini et al., 1990. J. Bacteriol. 172:2996–3002; Savioz et al., 1990. Gene 86:107–111; Brandriss and Falvey, 1992. J. Bacteriol. 174:3782–3788; Dougherty et al., 1992. Mol. Gen. Genet. 221:299–305; Williamson and Slocum, 1992. Plant Physiol. 100:1464–1470; Verbruggen et al., 1993. Plant Physiol. 103:771–781; Hoshino et al., 1994. Biochem. Biophys. Res. Comm. 199:410–417; Davis et al., 1995. Mol. Gen. Genet. 248:341–350).

To determine if a gene is involved in a given pathway, the gene is inactivated by a technique called "gene disruption". The gene is first disrupted in vitro on a plasmid. This is frequently accomplished (but not limited to) by inserting a selectable marker for transformation into an essential part of the gene or by deleting a region of the gene and substituting a selectable marker for transformation. Subsequently, the disrupted DNA is introduced into the organism by DNA-mediated transformation techniques. Often, the disrupted DNA is introduced into the organism as a linear molecule. The linear ends have homology to the genomic DNA and recombination between the disrupted plasmid DNA and the genomic DNA takes place whereby the genomic DNA is replaced by the disrupted plasmid DNA. DNA-mediated transformation technology has previously been developed for *Zalerion arboricola* (Kelly et al.1994. Curr. Genet. 26:217–224). It should be possible to apply this technology to the introduction of disrupted DNA into the organism. Gene disruptions have been accomplished in several filamentous fungi (Hoskins et al., 1990. Curr. Genet. 18:523–530; May, 1992. Fungal technology. Kinghorn, J. R., and Turner, G. (Eds.). Applied molecular genetics of filamentous fungi. Blackie Academic and Professional, Glasgow, UK, p.1–27; Sweigard et al., 1992. Mol. Gen. Genet. 232:183–190; Stahl and Schafer, 1992. The Plant Cell 4:621–629).

SUMMARY OF THE INVENTION

The present invention relates to the isolation of the gene which encodes an enzyme in the biosynthetic pathway of proline in *Zalerion arboricola*.

The invention also relates to the use of the gene to construct strains of *Z. arboricola* which produce less of an unwanted homologue of the desired pneumocandin product.

The invention further relates to the use of the gene in producing a strain of *Z. arboricola* which produces the desired pneumocandin product in high yield.

BRIEF DESCRIPTION OF THE DRAWINGS

FIG. 3 represents the nucleotide sequence of the cDNA insert from pPR2 encoding P5CR from *Z. arboricola* and the predicted peptide of the P5CR-encoding gene. (SEQ ID No. 1)

DETAILED DESCRIPTION OF THE INVENTION

The present invention relates to the isolation of the gene which encodes an important enzyme in the biosynthetic pathway of proline.

The first aspect of the invention relates to a gene encoding P5C reductase in order to determine if P5C reductase is involved in pneumocandin $A_0$ biosynthesis. If so, the manipulation of this gene may be important in modifying strains of Z. arboricola in order to produce the desired pneumocandin as the major product of the fermentation of Z. arboricola.

A second aspect of the invention relates to the use of the newly discovered gene to produce the desired pneumocandin, pneumocandin $B_0$.

A third aspect of the invention relates to a method of isolating the gene which comprises (a) isolating mRNA from Zalerion arboricola;

(b) reverse transcribing the mRNA of step (a) to construct a cDNA library in a S. cerevisiae expression vector;

(c) transforming the cDNA library of step (b) into a pro3 P5CR deficient proline-requiring mutant of S. cerevisiae;

(d) purifying the plasmid DNA from the S. cerevisiae transformant(s) that grow without proline resulting from step (c);

(e) hybridizing the isolated plasmid DNA containing cDNA from step (d) with genomic DNA; and (f) purifying the hybridized DNA of step (e).

Plasmids pPR2 and pPR4 have been deposited under the Budapest Treaty in the culture collection of the American Type Culture Collection, 12301 Parklawn Drive, Rockville, Md. 20852 on July 25, 1995 and assigned accession numbers ATCC 69872 and 69873, respectively.

Strains and DNA were isolated and handled by standard procedures (J. Sambrook, E. F. Fritsch, and T. Maniatis, "Molecular Cloning, A Laboratory Manual", second edition, Cold Spring Harbor Laboratory Press, Cold Spring Harbor, N.Y. (1989), referred to as Maniatis. Many of the procedures for working with S. cerevisiae are described in M. D. Rose, F. Winston, and P. Hieter, "Methods in Yeast Genetics: a Laboratory Course Manual", Cold Spring Harbor Laboratory Press, Cold Spring Harbor, N.Y. (1990), referred to as MYG.

The gene was isolated in the following manner.

EXAMPLE 1

(a) Isolation of P5C reductase cDNA clones

The proline auxotrophy of a S. cerevisiae P5CR (pro3) mutant, DT1100 (MATe ura3-52 trp1 pro3::TRP), was complemented with a Z. arboricola cDNA (DNA complementary to RNA) library that was constructed in the S. cerevisiae expression vector pYES2. The strain DT1100 has a deletion of all of the coding sequence of P5C reductase after codon 83 and was provided by Dr. Marjorie Brandriss, UMDNJ, Newark, N.J. (Tomenchok and Brandriss, 1987. J. Bacteriol. 169: 5364–5372). Plasmid pYES2 (obtained from In Vitrogen, San Diego, Calif., USA) replicates in both S. cerevisiae and E. coli and contains the following Saccharomyces sequences: an inducible GAL1 promoter linked to the multiple cloning site, CYC1 termination site, URA3 gene, and 2 micron origin of replication. Since genes from filamentous fungi usually contain introns (May, 1992. Fungal technology. Kinghom, J. R., and Turner, G. {Eds.}. Applied molecular genetics of filamentous fungi. Blackie Academic and Professional, Glasgow, UK, p.1–27), a cDNA library was selected for complementation.

Construction of a cDNA expression library necessitated development of a procedure for isolation of intact mRNA to use as template for cDNA synthesis. Protocols for RNA isolation had not been reported for Z. arboricola. The MRNA used for template for cDNA synthesis was isolated from mycelia of wild-type ATCC 20868. ATCC 20868 was obtained as described by Schwartz et al., 1989 (J. Antibiotics 42:163–167). For mRNA isolation, fifty-ml of KF seed medium (Schwartz et al., 1989. J. Antibiotics 42: 163–167) were inoculated with three ml of a vegetative mycelial stock (stock was mycelia in 10% glycerol that had been stored frozen at −80° C.) and grown for 48 hours at 25° C. with shaking at 220 rpm. The culture was washed and resuspended in a volume of water equal to the initial culture volume. Two ml of the suspension was used to inoculate 50 ml of RCMPA medium in 250 ml flasks (Kelly et al., 1994. Curr. Genet. 26: 217–224) and incubated in the same manner for 24 hours. Mycelia were collected by filtration over Miracloth (Calbiochem, La Jolla, Calif.), washed once with water, and frozen in liquid nitrogen. After lyophilization overnight, the mycelial pads were ground in a Waring blender with 10 ml guanidinium solution/g wet weight mycelia. Guanidinium solution contained 5M guanidimuium isothiocyanate, 0.05M Tris-HCl, pH7.5, 0.01M $Na_2EDTA$, 5% β-mercaptoethanol, 0.5% sodium lauroyl sarcosine, and 0.33% Antifoam A. The mixture was homogenized several times with a Dounce homogenizer and centrifuged at 10,000 rpm at 12° C. for ten minutes. The supernatant was extracted two times with phenol/chloroform/isoamyl alcohol-25:24:1, followed by an extraction with chloroform/isoamyl alchohol-24:1. Precipitation of the RNA was carried out overnight at −20° C. with 1/10 volume of 3M sodium acetate and 2.5 volumes of ethanol. The pellet was collected by centrifugation at 10,000 rpm at 4° C. for 20 minutes, macerated in 80% ethanol, and centrifuged again. Subsequently, the pellet was resuspended in 7.5 ml stock buffer (part of the "Fast Track" mRNA isolation kit of In Vitrogen, San Diego, Calif.) per g wet weight of mycelia. The mixture was sheared four times with a 21 gauge needle and isolation of mRNA proceeded according to the instructions of the kit with the following modifications. One oligo(dT) tablet was used per two grams wet weight mycelia and three additional low salt washes were added. The yield of mRNA was approximately 2–3 micrograms per gram wet weight mycelia. The mRNA appeared intact as demonstrated by Northern blot hybridization to the Neurospora crassa β-tubulin gene (data not presented) and yielded cDNA with a bulk size distribution of 0.8–5.0 kb.

An oligo(dT)-primed unidirectional cDNA library was constructed in pYES2 such that the cDNA inserts were linked to the GAL1 promoter. The library was constructed using a kit and instructions provided by the vendor In Vitrogen (San Diego, Calif.). The cDNAs were ligated to pYES2 that was digested with BstX1 and NotI. All of the cDNA inserts were in the same orientation, i.e., unidirectional. DT 1100 was transformed with the cDNA library by standard spheroplasting techniques (MYG). $Ura^+Pro^+$ transformants, i.e., transformants that can grow in the absence of uracil and proline, were selected on synthetic medium, which was osmotically stabilized with 1M sorbitol, and contained 2.0% galactose as the carbon source but lacked uracil and proline. The medium was solidified with 2.0% agar. The synthetic medium was Yeast Nitrogen Base without amino acids and without ammonium sulfate (Difco) supplemented with 0.2% ammonium sulfate. The Ura$^+$Pro$^+$ transformants were subsequently purified on the same medium. Plasmid DNA was isolated from two Ura$^+$Pro$^+$ transformants (MYG) and introduced into *E. coli* DH5alpha (GIBCO BRL, Gaithersburg, Md.). Plasmid DNA was prepared from ampicillin-resistant *E. coli* using the QIAGEN-tip 500 procedure (QIAGEN Inc., Chatsworth, Calif.). The resulting plasmids were designated pPR1 and pPR2. The ability of pPR1 and pPR2 to complement the pro3 mutation was confirmed by spontaneous curing of the plasmid in the original transformant. Curing restored the proline requirement. Retransformation of pPR1 and pPR2 into DTI 100 restored the Pro$^+$ phenotype. The resultant transformants were designated TR1 (pPR1) and TR2 (pPR2) and were further characterized.

(b) Characterization of cDNA inserts

Additional evidence that the Pro$^+$ phenotype of TR1 and TR2, i.e., ability to grow in the absence of proline, was due to pPR1 and pPR2 was provided by their poor growth on glucose-containing medium. The cDNA inserts were cloned under the control of the GAL1 promoter and it was expected that the transformants would be proline-requiring on glucose-containing medium since the GAL1 promoter is repressed by glucose. TR1, TR2, TRY (a transformant containing only vector pYES2), and another control, MB 1433, the Pro$^+$ parent of DT1100 (MATαtrp1 ura3-52, provided by M. Brandriss, UMDNJ; Tomenchok and Brandriss, 1987. J. Bacteriol. 169:5364–5372) were streaked onto synthetic medium with either 2.0% glucose or 2.0% galactose as the carbon source and solidifed with 2.0% agar. Transformants containing pPR1 and pPR2 did not grow well on glucose-containing medium, in contrast to the wild-type parent. The transformant containing only pYES2 did not grow on either medium.

That pPR1 and pPR2 enabled DTI 100 to grow in the absence of proline by restoring P5CR activity was confirmed by assaying the enzyme. P5CR activity was assayed by monitoring the oxidation of NADPH spectrophotometrically as detailed below in Table 1. P5CR activity was restored in TR 1 and TR2; they had substrate-dependent specific activities of 33 and 68 respectively, compared to 7.0 for TRY and 450 for the wild-type strain. The specific activity obtained for TR2 was double the value determined for TR1, and in fact, TR2 grew better than TR1 on galactose-containing medium.

TABLE I

P5CR activity in transformants of *S. cerevisiae* pro3 mutant containing *Z. arboricola* P5CR gene.

| Strain [plasmid][a] | Relevant[b] phenotype | P5CR activity[c] (nmol NADP/mg protein/min) |
|---|---|---|
| TRY [pYES2] | Pro$^-$ | 7.0 |
| TR1 [pPR1] | Pro$^+$ | 33.0 |
| TR2 [pPR2] | Pro$^+$ | 68.0 |
| MB1433 | Pro$^+$ | 450.0 |

[a]TRY, TR1, and TR2 are transformants of pro3 mutant DT1100. Plasmids and their origins are described in section a. MB1433 is described in section b.
[b]Relevant phenotype as determined on galactose-containing medium.

TABLE I-continued

P5CR activity in transformants of *S. cerevisiae* pro3 mutant containing *Z. arboricola* P5CR gene.

| Strain [plasmid][a] | Relevant[b] phenotype | P5CR activity[c] (nmol NADP/mg protein/min) |
|---|---|---|

[c]Specific activity was determined by subtracting the activity found in the absence of P5C from the activity found in the presence of P5C and was dependent upon the addition of exogenous NADPH. For preparation of extracts for enzyme activity, cultures were grown to an A$_{600}$ nm of 1.0 in synthetic broth medium containing 2.0% galactose as carbon source. TR1, TR2, and TRY were grown in the absence of uracil to maintain selective pressure for the transforming plasmid. The cells were broken with a mini Bead Beater (BioSpec, Bartlesville, OK, USA) by beating three times for 30 seconds using 0.5 mm glass beads with 30 second intervals of cooling. The unbroken cells were collected by centrifugation and the extracts were processed and assayed essentially as described by Brandriss, 1979 (J. Bacteriol. 138:816–822). Protein concentration was determined by the method of Bradford, 1976 (Anal. Biochem. 72:248–254), using a Bio-Rad reagent (Richmond, CA, USA).

Figure 2:
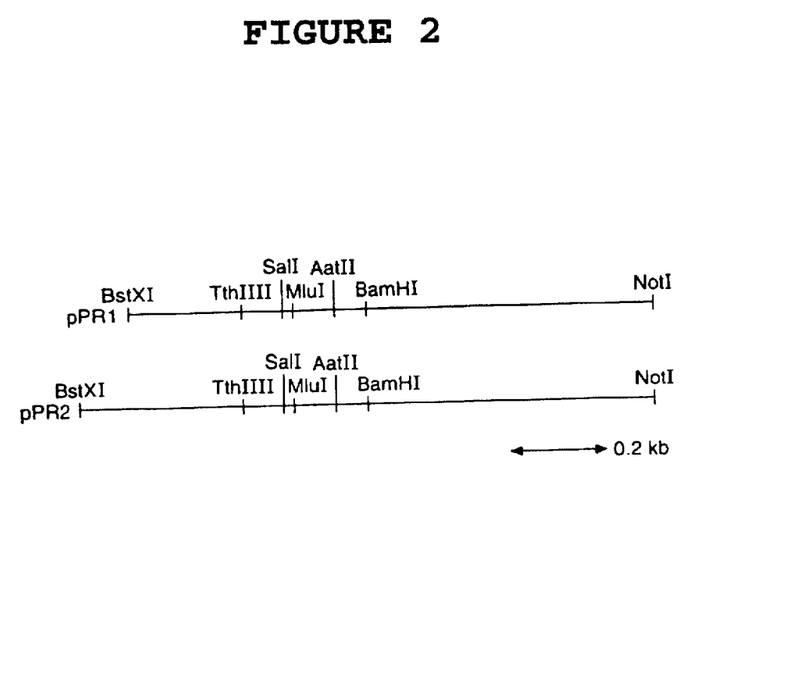
FIG. 2 represents restriction maps of *Z. arboricola* cDNA inserts of pPR1 and pPR2.

Plasmids pPR1 and pPR2 were digested with various combinations of restriction endonucleases and analyzed by agarose gel electrophoresis. The results showed that pPR1 and pPR2 were overlapping clones that contained inserts of ~1.1 and 1.2 kb. The major difference between the clones is that the insert of pPR2 is longer at the 5' end (FIG. 2). Thus, the mRNA encoded by pPR2 may have additional untranslated 5' sequence that is important for maximal expression and therefore may result in a higher specific activity. That the mRNA corresponding to the cDNA was expressed was determined by Northern blot hybridization. The mRNA from *Z. arboricola* ATCC 20868 was isolated and separated on a 1.5% agarose gel containing 6% formaldehyde and 1×MOPS buffer (20 mM MOPS, 5 mM sodium acetate, 1 mM EDTA, pH 7.0) with a 0.24–9.5 kb RNA ladder (GIBCO BRL, Gaithersburg, Md.) included as molecular weight standard. The gel was transferred to a Nytran nylon membrane (Schleicher and Schuell, Keene, N.H.) and hybridized according to a protocol of Gelman Sciences (Protocol Number 6, Application Protocols for BioTrace Binding Matrices). The probe was isolated by digestion of pPR1 with BstXI and NotI and radiolabeled with $^{32}$P by random priming using a kit and conditions recommended by the vendor Stratagene (La Jolla, Calif., USA). pPR1 was chosen as the source of the probe as the cDNA insert had less poly(T) (complementary to the poly (A) tail of the mRNA template) than the insert of pPR2 (data not presented). It was thought that a longer stretch of poly (T) might enable the probe to hybridize to multiple messages. A single ~1.1 kb mRNA was detected in wild-type *Z. arboricola* ATCC 20868 indicating that the P5CR gene was indeed expressed (data not presented).

To determine if *Z. arboricola* has only a single gene for P5CR, Southern blot analysis was performed. Genomic DNA was isolated using methods known to the art as described previously (Kelly et al., 1994, Curr. Genet. 26:217–224). Genomic DNA was isolated from both wild-type ATCC 20868 and ATCC 20957, a strain that produced substantially less pneumocandin A$_0$ (Masurekar et al., 1992, J. Antibiotics 45:1867–1874). The genomic DNAs were digested with restriction enzymes, the resultant fragments were separated by agarose gel electrophoresis, and the gel was transferred to a Nytran nylon membrane (Schleicher and Schuell, Keene, N.H.). The gel blot was hybridized to the radiolabeled cDNA insert of pPR1 prepared as described above for the Northern blot hybridization. The hybridization conditions were stringent and have been described previously (Kelly et al., Mol. Cell. Biol. 7:199–208). Two BamHI restriction fragments were detected, consistent with the single BamHI site in the insert, and single PstI and HindIII fragments were detected (data not presented). The data suggest that a single copy of the gene is present in each strain and that the strains were identical for the restriction enzymes tested.

(c) Sequence analysis and comparison

The nucleotide sequence of both strands of the cDNA insert of pPR2 was determined by the method of Sanger et al., 1977. (Proc. Natl. Acad. Sci. 74: 5463–5467), with the double-stranded sequencing protocol of a Sequenase kit, version 2.0 (US Biochemical, Cleveland, Ohio). The sequencing was initiated in both directions with primers complementary to vector sequence. As Z. arboricola sequences were identified, new primers were prepared to extend the sequence. The sequence is displayed in FIG. 3. The first ATG was presumed to be the translational start site as substantial homology to the amino acid sequence of other P5CRs was found between the first two methionines. In addition, the first ATG is the translational start site of most genes (Kozak, 1984. Nucleic Acids Res. 12: 857–872) and the sequence surrounding this ATG conformed to the "Kozak AUG initiator consensus motif" with a G at +4 and an A at −3 (Kozak, 1981. Nucleic Acids. Res. 9: 5233–5251). A single open reading frame of 0.96 kb was determined encoding a putative protein of 320 amino acids that is ~35 kD. The open reading frame of the Z. arboricola P5CR was compared to the amino acid sequences of P5CRs from several organisms in the data base including: Saccharomyces cerevisiae; Glycine max; Pisum sativum; Homo sapiens; Escherichia coli; Pseudomonas aeruginosa; Thermus thermophilus; Treponema pallidum; and Methanobrevibacter smithi. The comparisons were done with the GAP program of the University of Wisconsin Genetics Computer Group sequence analysis software package. The percent identity and similarity between the Z. arboricola P5CR and those of other species ranged from 24–39 and 50–57, respectively. The Z. arboricola P5CR exhibited the most identity, 39%, to the other fungal enzyme, P5CR from S. cerevisiae. None of the other P5CRs compared were more homologous to one another with the exception of the plant P5CRs which exhibited ~78–85% identity. A multiple sequence alignment of the P5CRs (performed using the "PileUp program of the University of Wisconsin Genetics Computer Group sequence analysis software package") indicated that numerous short blocks of amino acids throughout the proteins are highly conserved, and this is also true of P5CR from Z. arboricola. (data not presented). Thus, collectively all of the data support the contention that we have isolated a P5CR gene from Z. arboricola.

The second aspect of the invention relates to the use of the newly discovered gene to produce the desired pneumocandin, pneumocandin $B_0$. Pneumocandin $B_0$ is the precursor of a potent semi-synthetic antifungal compound. Through genetic manipulation of the gene encoding P5CR, strains devoid of impurities and/or strains producing improved titers of pneumocandin $B_0$ can be prepared. One of the steps in the biosynthesis of pneumocandin $A_0$ is similar to the reaction catalyzed by P5C reductase. Therefore, disrupting the gene encoding P5C reductase could create a strain devoid of the undesired pneumocandin $A_0$. Additionally, exogenous proline has been shown to increase titers of pneumocandin $B_0$ and thus overexpression of the P5C reductase gene could increase proline levels and hence production of pneumocandin $B_0$.

Gene disruptions are usually performed with genomic clones; compared to a cDNA clone, disruption of a genomic clone has the advantages of (1) more sequence for targeting the disrupted DNA to its chromosomal location (2) better alignment with the chromosomal DNA. Many genes of filamentous fungi contain introns and hence alignment of homologous sequence may require looping out of genomic DNA. In addition, the cDNA has sequences representing the poly(A) tail of the mRNA which is a posttranscriptional modification that would not be specifically homologous to genomic P5CR DNA. Therefore, we isolated a genomic clone by cross hybridization using the cDNA as a probe.

EXAMPLE 2 a) Isolation of genomic P5C reductase clone

Isolation of a genomic P5C reductase clone necessitated the construction of a genomic library which could be used to screen for genes by cross-hybridization. The library was constructed in the vector "Lambda Dash 11" (Stratagene, La Jolla, Calif.). The overall strategy was to insert ~20 kb partial Sau3A restriction fragments of Z. arboricola genomic DNA into Lambda Dash II arms prepared by digestion with BamHI. Genomic DNA from Z. arboricola was isolated using methods known to the art as described previously (Kelly et al., 1994. Curr. Genet. 26:217–224). The Lambda Dash II arms digested with BamHI were obtained from Stratagene (LaJolla, Calif.). A packaging extract obtained from Stratagene that preferentially size selects for recombinants with large inserts was employed. The library was constructed as follows. Conditions were optimized to obtain ~20 kb Sau3A partial restriction fragments of Z. arboricola genomic DNA. Restriction fragments with a bulk size distribution between 20–40 kb were obtained with 0.014 units Sau3A/μg DNA following one hour incubation at 37° C. The DNA was subsequently dephosphorylated to prevent the self-ligation of smaller fragments which could form a molecule large enough to be packaged. This was accomplished by incubation with calf-intestinal alkaline phosphatase (capping, Maniatis). The effectiveness of the dephosphorylation was determined by monitoring the self-ligation of capped and uncapped partial fragments. Only the capped DNA did not self-ligate as determined by agarose gel electrophoresis. Approximately 0.5 μg of the dephosphorylated Sau3A partial digest was ligated to 1.2 μg lambda arms with T4 DNA ligase, and that ligation had occurred was confirmed by gel electrophoresis. Subsequently, a portion of the ligated DNA was packaged in vitro utilizing a Gigapack XLII packaging extract (Stratagene, LaJolla, Calif.). This extract will package a 20 kb insert with a 95% greater efficiency than a 14 kb insert according to the vendor. E coli P2392 was chosen as the host for infection with the recombinant phage to eliminate the selection of recombinants containing the lambda stuffer fragment. Preparations of the lambda arms are not entirely devoid of the stuffer fragment. P2392 contains prophage P2 which restricts the growth of wild-type lambda, unless the red and gam genes are absent. Red and gam genes are present in the stuffer fragment of Lambda Dash II, hence the phage will not grow. E. coli P2392 was also obtained from Stratagene (LaJolla, Calif.). All protocols for handling the phage were according to the vendor Stratagene and were based on methods known in the art (Maniatis). P2392 was made competent and infected with a portion of the phage and $5 \times 10^5$ plaque forming units were obtained. The phage were harvested and the library was subsequently amplified. The titer of the library following amplification was approximately $1 \times 10^7$ pfus per ml. The insert sizes of five recombinant phage were determined by restriction analysis. Minipreparations of lambda DNA were prepared from five plaques using the QIAGEN-tip 20 procedure (QIAGEN Inc., Chatsworth, Calif.) and digested with EcoRI. The results indicated an average insert size of 20 kb and that each phage had a different restriction pattern.

The lambda library was subsequently screened by plaque hybridization. Plaque lifts were prepared on Nytran membranes according to the directions of the manufacturer (Schleicher and Schuell) using methods known to the art (Maniatis). Each 150 mm filter contained approximately 5000 plaques. The filters were hybridized under stringent conditions to the 1.1 kb BstXI-NotI insert of pPR1 that was radiolabeled by random priming (Maniatis). Eleven out of 15,000 plaques screened hybridized to the probe with various intensities. Positive plaques were picked and the phage were eluted into SM broth. Plaque lifts of each isolate were prepared and hybridized to the insert of pPR1 again in a secondary screen. Six out of the eleven initial isolates were positive. Another round of plaque purification and hybridization was carried out with the 6 positive isolates. Five of the phage hybridized strongly and plate phage stocks were prepared from single plaques (#s 1, 2, 3, 4, and 11) and subsequently titred. Lambda DNA was isolated from the phage using the QIAGEN-tip 500 procedure (QIAGEN Inc., Chatsworth, Calif.).

Subsequently, two of the clones (#1 and #2) were determined to be identical by restriction analysis of the DNA. Southern blot analysis confirmed that all of the clones hybridized to the cDNA probe. To localize the putative P5C gene on the lambda clones, DNA from the clones was digested with three enzymes which do not cut the vector DNA: HindIII, SstI, and XhoI. The Zalerion DNA is cloned at the BamHI site in place of the 14 kb stuffer fragment. Genomic DNA was also digested with the same enzymes and gel blots were hybridized to a cDNA insert containing the putative P5C reductase gene of pPR1. With clone 4, a single XhoI, HindIII, and SstI fragment was obtained that was the same size as the genomic fragment, suggesting that the P5C gene on clone 4 is flanked with more Zalerion DNA than in the other clones. Thus, clone #4 was chosen for further work.

Figure 4A:
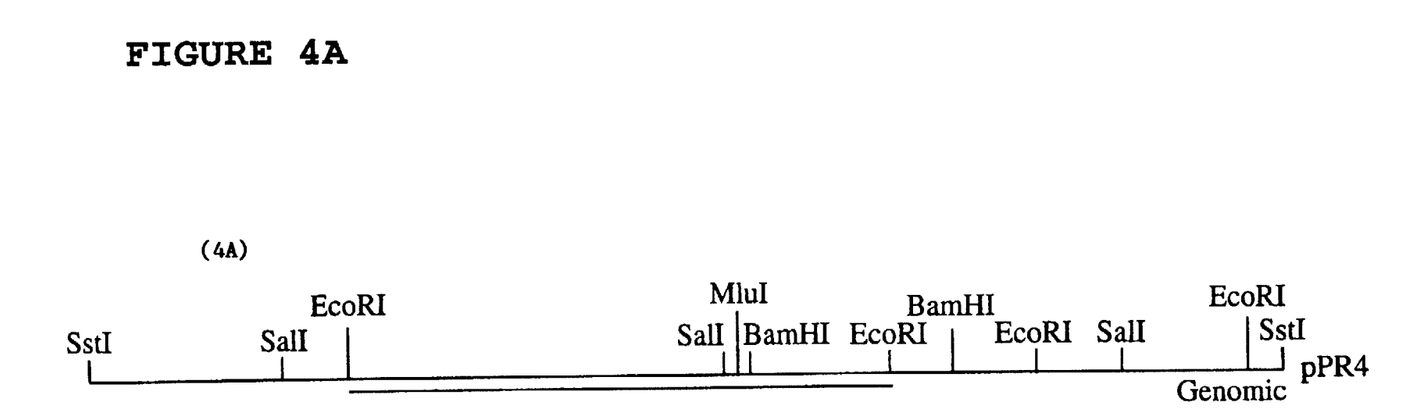
FIGS. 4a and 4b represent a comparison of the restriction maps of the genomic insert of pPR4 and the cDNA insert of pPR2. The 3.1 kb EcoRI fragment of pPR4 that hybridized to the cDNA insert is shown.
Figure 4B:
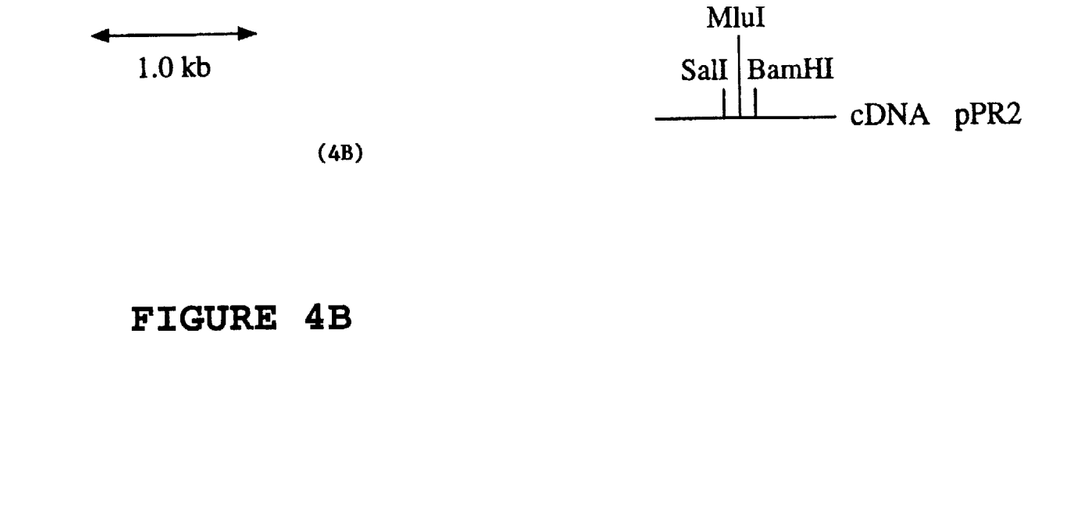

Two subclones were constructed from lambda genomic clone #4: an ~7 kb HindIII fragment and an ~8 kb SstI fragment that demonstrated hybridization to the cDNA probe were subcloned onto Bluescript SK+ vector (obtained from Stratagene, La Jolla, Calif.) to create plasmids pPR3 and pPR4, respectively. Restriction analysis indicated that pPR3 and pPR4 contained approximately 5.6 kb of overlap and that plasmid pPR3 was longer at the 5' end and plasmid pPR4 was longer at the 3' end. The P5CR gene was localized on the genomic clones by Southern blot hybridization to the cDNA insert of pPR1. The hybridizing region was contained on a 3.1 kb EcoRI fragment found in both pPR3 and pPR4. Within the hybridizing region of the genomic clone are restriction sites identical to those of the cDNA clone, confirming that the correct genomic clone was isolated. A comparison of the restriction maps of cDNA clone pPR2 and genomic clone pPR4 is shown in FIG. 4. Colinearity of the genomic clones with genomic DNA was also confirmed by Southern blot hybridization. For subclone pPR3, the expected HindIII and HindIII-BamHI fragments were obtained; for subclone pPR4 the expected SstI, SalI, and SstI-PstI fragments were detected (data not presented).

b) Disruption of the P5CR gene

The first step involved in disrupting the P5CR gene of Z. arboricola would be to inactivate the gene in vitro. The P5CR gene is inactivated in vitro on plasmid pPR4 which contains the genomic P5CR gene centrally located with at least ~3.0 kb of flanking sequence on both sides. The large amount of flanking sequence should facilitate targeted gene replacement when the disrupted plasmid DNA is introduced into Zalerion. In order to inactivate the putative P5CR gene, a deletion of P5CR sequence could be made using an exonuclease that deletes progressively in both directions. Subsequently, a selectable marker for transformation is inserted at the site of the deletion, further interrupting the gene. The MluI site of pPR4 is a convenient site to target the deletion. Deletions initiated at the MluI site and ranging from ~250 to ~600 nucleotides would encompass only the P5CR gene. This range of deletions would delete between 84 to 200 amino acids. These are substantial deletions for a protein of 320 amino acids. It is expected that deletion of only 84 amino acids would inactivate the gene based on the following evidence.

The cDNA encoding P5CR on pPR2 was inactivated in vitro by insertion of a 2.4 kb SalI-SalI fragment of pCSN43 into the SalI site of P5CR to construct pPR2HY. The 2.4 kb SalI-SalI fragment contains a hygromycin B resistant gene which is the hygromycin phosphotransferase gene from E. coli under the control of A. nidulans trpC transcription signals. Plasmid pCSN43 was obtained from the Fungal Genetics Stock Center (Kansas City, Kans.). Plasmid pPR2HY was transformed into DT1100 as described in section a and Ura+ transformants (transformants able to grow in the absence of uracil) were selected. The transformants were subsequently tested for growth in the absence of proline. No growth was obtained, indicating that the proline auxotrophy was not complemented by the disrupted plasmid. This result indicates that insertion of a marker gene into the SalI site of the cDNA encoding P5CR is sufficient to inactivate function of the gene in S. cerevisiae.

The MluI site of P5CR is adjacent to the SalI site and in fact, the two restriction sites overlap as indicated by the sequence analysis (a restriction map was generated using the MAP program of the University of Wisconsin Genetics Computer Group sequence analysis software package). Thus it is highly likely that mere insertion of a selectable marker into the MluI site will inactivate P5CR and further deletion of amino acids would certainly inactivate the gene. The MluI site of pPR4 is chosen for the site of the disruption, rather than the SalI site, as the MluI site is unique in pPR4. Plasmid pPR4 is linearized by digestion with MluI and treated with exonuclease III to create single stranded deletions in both directions. The deletions are made using reagents and instructions of an ExoIII/Mung Bean Deletion kit obtained from the vendor Stratagene (La Jolla, Calif.). Incubation with mung bean nuclease will remove the single-stranded DNA and form blunt ends. Restriction enzyme digests of pPR4 treated with exonuclease III are compared to untreated pPR4 to confirm the size of the deletion. The plasmid containing the deleted DNA will be ligated with the 2.4 kb SalI-SalI fragment of pCSN43 containing the hygromycin B resistant cassette described above. It has previously been shown that this gene can be used as a selectable marker for transformation of Z. arboricola (Kelly et al., 1994. Curr. Genet. 26:217–224). Assuming a deletion of ~250 bp is made within P5CR of pPR4, ~4.3 and 3.9 kb of Zalerion DNA would remain flanking the disruption. The large amount of flanking sequence should facilitate targeted gene replacement when the disrupted DNA is released from the plasmid and transformed into the genome.

An SstI digest of this disrupted plasmid is introduced into wild-type Z. arboricola ATCC 20868 by DNA-mediated transformation as described (Kelly et al., 1994. Curr. Genet.

26: 217–224) using methods known to the art. Transformants resistant to hygromcyin are selected as described previously (Kelly et al., 1994. supra). The transformants can be assessed for a gene disruption of P5CR in several ways. The simplest and most direct way is to test to see if the transformants require proline for growth which is the expected phenotype. At least 500 hygromycin transformants are tested for a proline requirement, in the event that homologous recombination is low in Z. arboricola. Those transformants requiring proline for growth are further evaluated to determine if a gene replacement has occurred. This is assesed by Southern blot analysis. DNA from the transformants is digested with at least one restriction enzyme(s) that flanks the restriction site(s) used to target the plasmid DNA to the genome, and that would generate a unique fragment when hybridized to a P5CR probe. P5CR activity in the proline requiring transformants is also determined (Brandriss, 1979. J. Bacteriol. 138:816–822). Production of pneumocandins is also assessed in the proline requiring strains to determine if pneumocandin $A_0$ has been eliminated.

If none of the transformants require proline for growth, they are evaluated molecularly to determine if a gene replacement has occurred. It is not definitively known whether Z. arboricola is haploid or diploid, although there is some evidence to suggest that it is haploid (Kelly et al., 1994. Curr. Genet. 26: 217–224). If *Z. arboricola* is diploid and a gene replacement takes place on one homolog, there will probably be no discernible phenotype and it will be necessary to analyze the DNA. This is accomplished in several ways. One approach is to assess homologous recombination by Southern blot analysis as described above. This is a standard method known to the art for assessing whether or not a gene replacement has occured. An alternative method, and one that is advantageous for evaluating a large number of transformants, is to use a PCR (polymerase chain reaction) assay. This method has the advantage that small amounts of DNA can be used, and the DNA does not have to be as high molecular weight as it does for Southern blot analysis. DNA is isolated from mycelia in a small scale as described by Lee and Taylor, 1990. (PCR Protocols: A Guide to Methods and Applications, Innis, M., Gelfand, D., Snisnsky, J., and White, T. {Eds.} Academic Press, Inc., San Diego, Calif., p.282–287). Primers for PCR are designed such that the forward primer is complementary to the *Z. arboricola* sequence upstream of the 5' restriction site used to target the disrupted DNA, and the reverse primer would be complementary to the sequence within the hygromycin resistant cassette. An example of this approach to detect a gene disruption is described by Aufauvre-Brown et al.,1993 (Curr. Genet., 1993. 24:177–178).

If the results indicate that there are two chromosomal homologs and if a strain with a gene disruption on one homolog is identified, then this transformant would be further mutagenized to inactivate the copy of the gene on the other homolog. This is most readily accomplished using chemical mutagenesis as disclosed in example 1 of U.S. Pat. No. 5,162,211 issued Nov. 10, 1992 to Sesin et al. and example 1 of U.S. Pat. No. 5,366,880 issued Nov. 22, 1994 to Schwartz et al. The resulting mutagenized colonies would be screened for a proline requirement and analyzed as described above.

EXAMPLE 3

Overexpression of the P5CR gene

One approach to overexpress the P5CR gene is based on the previous observation that transformation of *Z. arboricola* with a plasmid containing the hygromycin resistance conferring cassette, i.e., pCSN43, resulted in the integration of multiple copies of the transforming DNA in the majority of transformants tested (Kelly et al., 1994. Curr. Genet. 26:217–224). Thus, plasmids are constructed that contain the hygromycin resistant conferring cassette and the P5CR genomic gene. One example is to subclone the hygromcyin resistant conferring cassette onto pPR4 which contains the genomic clone of P5CR using methods known to the art (Maniatis). It is also possible to isolate a fragment of pPR4, such as the 3.1 kb EcoRI-EcoRI fragment that hybridized to the cDNA and that most likely contains the entire P5CR gene, onto pCSN43. An example of the former is as follows. The hygromycin resistant conferring cassette is isolated from pCSN43 as a 2.4 kb SalI-SalI fragment. pPR4 is digested with XbaI. Both the 2.4 kb SalI-SalI fragment and the pPR4 XbaI digest are treated with T4 DNA polymerase to form blunt ends, are ligated, and subsequently transformed into *E. coli.* The resultant plasmid is transformed into *Z. arboricola* ATCC 20868 and hygromycin resistant transformants are selected as described previously (Kelly et al., 1994., supra). The hygromycin resistant transformants are assessed by Southern blot and DNA slot blot analysis using methods known to the art to determine if multiple copies of the P5CR gene were introduced into *Z. arboricola.* Transformants containing multiple copies of P5CR are assayed for P5CR enzyme activity as detailed by Brandriss, 1979 (J. Bacteriol. 138:816–822). The hygromycin resistant transformants are subsequently assessed for pneumocandin production to determine if increased levels of pneumocandin $B_0$ are produced.

Another approach is to clone the cDNA encoding P5CR under the control of a strong promoter from *Z. arboricola.* This involves isolating a strong promoter from *Z. arboricola.* Genes encoding the enzyme glyceraldehyde-3-phosphate dehydrogenase are constitutively expressed at a high level from many organisms and the promoter of this gene is frequently used for high levels of expression (Itoh et al., 1986. Biochem. Biophys. Res. Commun. 138: 268–274; Jungehulsing et al., Curr. Genet. 1944. 25: 101–106; Kimura et al., 1991. J. Ferm. Bioen. 71: 145–150.; Punt et al., 1987. Gene 56: 117–124). The predicted protein sequences of glyceraldehyde phosphate dehydrogenases are highly conserved (T. Smith, Proc. Natl. Acad. Sci, 1989. 86: 7063–7066) and the DNA sequences of glyceraldehyde phosphate dehydrogenases of several filamentous fungi are very similar (Van Wert and Yoder, 1992. Curr. Genet., 22:29–35). This makes gene isolation with a heterologous probe possible which is the approach used to isolate the glyceraldehyde phosphate dehydrogenase gene from several filamentous fungi (Choi and Nuss, 1990. Nucleic Acids Res. 18:5566; Jungehulsing et al.,Curr. Genet. 1944. 25: 101–106; Kimura et al., 1991. J. Ferm. Bioen. 71: 145–150.; Punt et al., 1988. Gene 69: 49–57).

The glyceraldehyde phosphate dehydrogenase gene from *Z. arboricola* is cloned as follows using methods known to the art (Maniatis) and described previously herein. The cloning strategy is to isolate the Zalerion gene by cross hybridization with a probe derived from the glyceraldehyde phosphate dehydrogenase gene of *Aspergillus nidulans.* The probe is a restriction fragment within the *A. nidulans* gene. Southern blots of genomic DNA from *Z. arboricola* are hybridized to the Aspergillus probe under either stringent or nonstringent conditions to demonstrate homology that is suitable to subsequently clone the gene. The *Z. arboricola* genomic library constructed in Lambda Dash II is subsequently screened with the Aspergillus probe in the same manner that the genomic P5CR gene was isolated. Positive clones are confirmed by DNA sequencing to ensure that the glyceraldehyde phosphate dehydrogenase gene has been isolated. The promoter of the gene (region upstream of the coding sequence) is identified and isolated by restriction digestion or PCR and cloned into a vector. The P5CR cDNA is subsequently linked to the promoter in the appropriate orientation. Next the hygromycin resistance conferring cassette is inserted into the vector. The resultant plasmid that contains the promoter of the glyceraldehyde phosphate dehydrogenase gene linked to the P5CR cDNA and that also contains the hygromycin resistance conferring cassette is transformed into *Z. arboricola* ATCC 20868. The resultant transformants are analyzed as described above.

---

What is claimed is:

1. An isolated gene coding for L-proline: NAD(P)$^+$5-oxidoreductase, EC 1.5.1.2 (delta$^1$-pyrroline-5-carboxylate reductase) from *Zalerion arboricola*.

2. An isolated gene as claimed in claim 1 which is contained in a cDNA fragment represented by a restriction enzyme map as specified in FIGS. 2 and 4b.

3. An isolated gene as claimed in claim 1 which is contained in a genomic DNA fragment represented by a restriction enzyme map as specified in FIG. 4a.

4. A recombinant plasmid containing a gene of claim 1.

5. A process for preparing a strain of *Zalerion arboricola* which produces pneumocandin B$_0$ in high titers comprising overexpressing the gene claimed in claim 1.

6. The process of claim 5 wherein the overexpression of the gene results in increased proline levels.

7. A process for preparing a strain of *Zalerion arboricola* which produces pneumocandins devoid of pneumocandin A$_0$ comprising disruption of the gene claimed in claim 1.

8. A strain of *Zalerion arboricola* produced by the process of claim 5.

9. A strain of *Zalerion arboricola* produced by the process of claim 7.

10. A method of isolating the gene claimed in claim 1 comprising (a) isolating mRNA from *Zalerion arboricola*;

(b) reverse transcribing the mRNA of step (a) to construct a cDNA library in a *S. cerevisiae* expression vector;

(c) transforming the cDNA library of step (b) into a pro3 P5CR deficient proline-requiring mutant of *S. cerevisiae*;

(d) purifying the plasmid DNA from the *S. cerevisiae* transformant(s) that grow without proline resulting from step (c);

(e) hybridizing the isolated plasmid DNA containing cDNA from step (d) with genomic DNA; and (f) purifying the hybridized DNA of step (e).

11. A transformed cell containing the gene claimed in claim 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1147 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 47..960

( x i ) SEQUENCE DESCRIPTION: SEQ ID NO:1:

```
TCGAATAATT GAAGTTCTTG ATCATTTAGG AGTCTGAAAA GTCAAG ATG GCA TCC         55
                                                   Met Ala Ser
                                                    1

ACA GCA AAG GAG GGG TCA GAA TTG ACT TTG GCG GTG ATA GGT TGT GGT       103
Thr Ala Lys Glu Gly Ser Glu Leu Thr Leu Ala Val Ile Gly Cys Gly
     5                  10                  15

ACA ATG GGC ATA GCA ATC CTC TCC GGT ATC CTA GCA TCT CTC GAC GAA       151
Thr Met Gly Ile Ala Ile Leu Ser Gly Ile Leu Ala Ser Leu Asp Glu
 20                  25                  30                  35

ATC CAC GCA CCA AAC TCG CAG TCC TCA GAG ACA GAC GAA ACA CCC TCA       199
Ile His Ala Pro Asn Ser Gln Ser Ser Glu Thr Asp Glu Thr Pro Ser
                 40                  45                  50

AAG CTC CCC ACC AAA TTC ATA GCC TGT GTC CGC TCA CCC AAA GGC GCA       247
Lys Leu Pro Thr Lys Phe Ile Ala Cys Val Arg Ser Pro Lys Gly Ala
             55                  60                  65

GAA AAG ATC AAA AAA GCA CTC TCA CCC TAC AAA ACC CCC GTC AAA ATC       295
Glu Lys Ile Lys Lys Ala Leu Ser Pro Tyr Lys Thr Pro Val Lys Ile
         70                  75                  80

ATC CAA AGC GAC AAT GTC ACC GCC TGT AGA GAG GCA GAT GTA GTA TTA       343
Ile Gln Ser Asp Asn Val Thr Ala Cys Arg Glu Ala Asp Val Val Leu
     85                  90                  95

CTA GGC TGT AAA CCA TAT ATG GCC GAA GGC ATA TTA GGC GAA GAG GGG       391
Leu Gly Cys Lys Pro Tyr Met Ala Glu Gly Ile Leu Gly Glu Glu Gly
100                 105                 110                 115

ATG GTC GAC GCG TTA AAG GGG AAA TTG TTG ATT AGC ATC CTA GCT GGC       439
Met Val Asp Ala Leu Lys Gly Lys Leu Leu Ile Ser Ile Leu Ala Gly
                120                 125                 130

GTT CCC GCA GAG CAG ATA TAC GGG TAC ATG TAC GGC AAA ACA CCA GTG       487
Val Pro Ala Glu Gln Ile Tyr Gly Tyr Met Tyr Gly Lys Thr Pro Val
            135                 140                 145

AAC CCA GAG AAA GAG GGA TTA TGT CAA GTC GTG CGA GCA ATG CCA AAT       535
Asn Pro Glu Lys Glu Gly Leu Cys Gln Val Val Arg Ala Met Pro Asn
```

-continued

```
             150                          155                          160
ACA  GCG  TCT  GGG  ATC  CGG  GAA  TCC  ATG  ACT  GTG  ATC  GCG  ACG  TCG  AGT        583
Thr  Ala  Ser  Gly  Ile  Arg  Glu  Ser  Met  Thr  Val  Ile  Ala  Thr  Ser  Ser
     165                 170                          175

CCC  CCA  TTA  TCA  GCT  ACA  ACT  TCG  AGT  CTG  ATA  ACC  TGG  ATC  TTC  AAA        631
Pro  Pro  Leu  Ser  Ala  Thr  Thr  Ser  Ser  Leu  Ile  Thr  Trp  Ile  Phe  Lys
180                      185                          190                 195

CGC  ATT  GGC  GAT  GTC  GTC  CAG  CTC  CCC  GCT  GCT  ACA  ATG  GAT  GCC  AGC        679
Arg  Ile  Gly  Asp  Val  Val  Gln  Leu  Pro  Ala  Ala  Thr  Met  Asp  Ala  Ser
                    200                      205                      210

ACC  GCG  CTG  TGT  GGC  AGT  GGC  CCA  GCC  TTT  TTT  GCG  CTC  ATA  CTG  GAG        727
Thr  Ala  Leu  Cys  Gly  Ser  Gly  Pro  Ala  Phe  Phe  Ala  Leu  Ile  Leu  Glu
               215                      220                      225

GCT  GCG  ATT  GAT  GGG  GCT  GTG  GCG  ATG  GGG  TTG  CCA  AGA  GCA  GAG  GCT        775
Ala  Ala  Ile  Asp  Gly  Ala  Val  Ala  Met  Gly  Leu  Pro  Arg  Ala  Glu  Ala
          230                      235                      240

CAG  AGA  ATG  GCG  GCG  CAG  ACT  ATG  AAA  GGG  GCT  GCT  GGA  TTG  GTA  TTG        823
Gln  Arg  Met  Ala  Ala  Gln  Thr  Met  Lys  Gly  Ala  Ala  Gly  Leu  Val  Leu
     245                      250                      255

TCT  GGA  GAG  CAT  CCG  GCG  TTG  CTG  AAA  GAT  AAA  GTG  ACT  ACG  CCG  GGT        871
Ser  Gly  Glu  His  Pro  Ala  Leu  Leu  Lys  Asp  Lys  Val  Thr  Thr  Pro  Gly
260                      265                      270                      275

GGG  TGC  ACG  ATA  GGT  GGG  CTG  ATG  GTG  CTG  GAA  GAA  GGA  GGG  GTG  AGA        919
Gly  Cys  Thr  Ile  Gly  Gly  Leu  Met  Val  Leu  Glu  Glu  Gly  Gly  Val  Arg
                    280                      285                      290

GGG  ACC  GTG  GCT  AGA  GCA  GTT  AGG  GAA  GCT  ACT  GTG  GTT  GC                   960
Gly  Thr  Val  Ala  Arg  Ala  Val  Arg  Glu  Ala  Thr  Val  Val
               295                      300

CAGTCAGCTT  GGTAAAGGGG  TTCAGGGAGT  CAACGGTACA  CGATTTTGAA  ACAGCCATAC               1020

TGCGTAGACA  CATGTCCAAG  GAGTTCTGGG  GTATAAAAAG  TTGTTCATTT  ATGAAAAAAA               1080

AAAAAAAAAA  AAAAAAAAAA  AAAAAAAAAA  AAAAAAAAAA  AAAAAAAAAA  AAAAAAAAAA               1140

AAAAAAA                                                                              1147
```

( 2 ) INFORMATION FOR SEQ ID NO:2:

( i ) SEQUENCE CHARACTERISTICS:
        ( A ) LENGTH: 304 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met  Ala  Ser  Thr  Ala  Lys  Glu  Gly  Ser  Glu  Leu  Thr  Leu  Ala  Val  Ile
 1                  5                        10                       15

Gly  Cys  Gly  Thr  Met  Gly  Ile  Ala  Ile  Leu  Ser  Gly  Ile  Leu  Ala  Ser
               20                       25                       30

Leu  Asp  Glu  Ile  His  Ala  Pro  Asn  Ser  Gln  Ser  Ser  Glu  Thr  Asp  Glu
          35                       40                       45

Thr  Pro  Ser  Lys  Leu  Pro  Thr  Lys  Phe  Ile  Ala  Cys  Val  Arg  Ser  Pro
     50                       55                       60

Lys  Gly  Ala  Glu  Lys  Ile  Lys  Lys  Ala  Leu  Ser  Pro  Tyr  Lys  Thr  Pro
65                       70                       75                       80

Val  Lys  Ile  Ile  Gln  Ser  Asp  Asn  Val  Thr  Ala  Cys  Arg  Glu  Ala  Asp
                    85                       90                       95

Val  Val  Leu  Leu  Gly  Cys  Lys  Pro  Tyr  Met  Ala  Glu  Gly  Ile  Leu  Gly
               100                      105                      110

Glu  Glu  Gly  Met  Val  Asp  Ala  Leu  Lys  Gly  Lys  Leu  Leu  Ile  Ser  Ile
```

```
                        115                         120                           125

Leu  Ala  Gly  Val  Pro  Ala  Glu  Gln  Ile  Tyr  Gly  Tyr  Met  Tyr  Gly  Lys
             130                      135                     140

Thr  Pro  Val  Asn  Pro  Glu  Lys  Glu  Gly  Leu  Cys  Gln  Val  Val  Arg  Ala
        145                      150                     155                          160

Met  Pro  Asn  Thr  Ala  Ser  Gly  Ile  Arg  Glu  Ser  Met  Thr  Val  Ile  Ala
                            165                     170                          175

Thr  Ser  Ser  Pro  Pro  Leu  Ser  Ala  Thr  Thr  Ser  Ser  Leu  Ile  Thr  Trp
                       180                     185                          190

Ile  Phe  Lys  Arg  Ile  Gly  Asp  Val  Val  Gln  Leu  Pro  Ala  Ala  Thr  Met
                  195                      200                          205

Asp  Ala  Ser  Thr  Ala  Leu  Cys  Gly  Ser  Gly  Pro  Ala  Phe  Phe  Ala  Leu
             210                      215                          220

Ile  Leu  Glu  Ala  Ala  Ile  Asp  Gly  Ala  Val  Ala  Met  Gly  Leu  Pro  Arg
        225                      230                     235                          240

Ala  Glu  Ala  Gln  Arg  Met  Ala  Ala  Gln  Thr  Met  Lys  Gly  Ala  Ala  Gly
                            245                     250                          255

Leu  Val  Leu  Ser  Gly  Glu  His  Pro  Ala  Leu  Leu  Lys  Asp  Lys  Val  Thr
                       260                     265                          270

Thr  Pro  Gly  Gly  Cys  Thr  Ile  Gly  Gly  Leu  Met  Val  Leu  Glu  Glu  Gly
                  275                      280                          285

Gly  Val  Arg  Gly  Thr  Val  Ala  Arg  Ala  Val  Arg  Glu  Ala  Thr  Val  Val
             290                      295                          300
```